United States Patent [19]

Marty

[11] Patent Number: 4,536,161
[45] Date of Patent: Aug. 20, 1985

[54] ARTICULATOR

[76] Inventor: Urs Marty, Stötzlistrasse 62, 8707 Uetikon am See, Schweiz, Switzerland

[21] Appl. No.: 599,410

[22] Filed: Apr. 12, 1984

[30] Foreign Application Priority Data

May 6, 1983 [CH] Switzerland ............... 2495/83

[51] Int. Cl.³ .............................................. A61C 11/00
[52] U.S. Cl. ...................................... 434/264; 433/58
[58] Field of Search .................................. 433/54–67; 434/264

[56] References Cited

U.S. PATENT DOCUMENTS 3,059,336 10/1962 Windish ........................ 433/54 X
3,772,788 11/1973 Gerber .
3,931,679 1/1976 Carter ................................ 434/264
4,365,955 12/1982 Tradowsky ................... 434/264 X

FOREIGN PATENT DOCUMENTS 346319 6/1960 Switzerland .
350757 1/1961 Switzerland .
412194 11/1966 Switzerland .
437629 11/1967 Switzerland .
515031 12/1971 Switzerland .
604675 9/1978 Switzerland .

Primary Examiner—Harland S. Skogquist
Attorney, Agent, or Firm—Panitch, Schwarze, Jacobs & Nadel

[57] ABSTRACT

An articulator in which all natural chewing movements (articulation) and the biting movement (occlusion) shall be simulated. To this end a fixture is positively guided by means of a spring loaded elongated shaft relative to a base in three degrees of freedom. The positive movement proceeds via the longitudinal shaft as well as slanted surfaces extending obliquely relative to the longitudinal shaft and additionally a cam member including a cam follower is provided which determine the path of movement in the three axes of the articulation. In order to allow the occlusion the fixture can be pivoted relative to the base around a lateral shaft.

9 Claims, 6 Drawing Figures

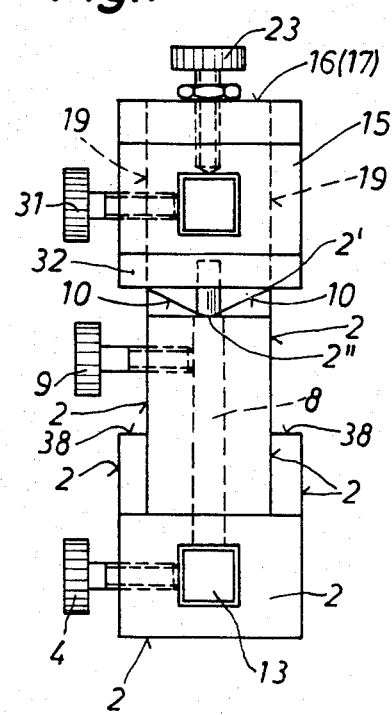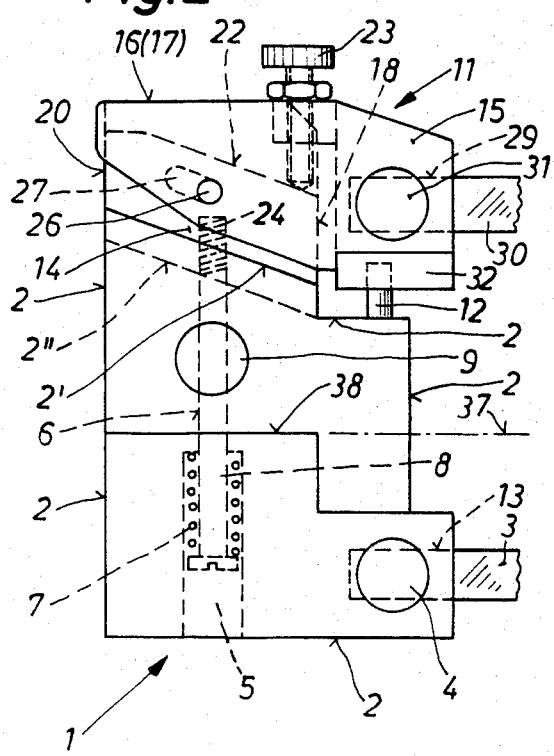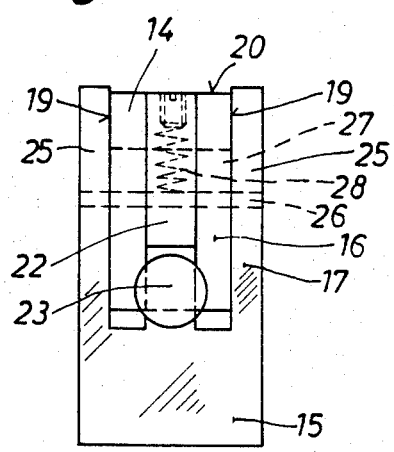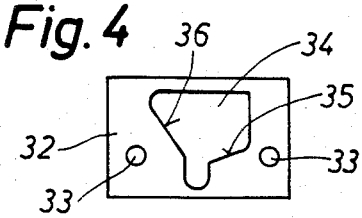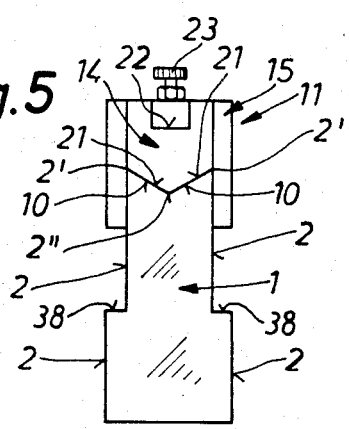

4,536,161

ARTICULATOR

BACKGROUND OF THE INVENTION

1. Field of the Invention

The present invention relates to an improved articulator having a base including a support for a model of a lower jaw, said support carried by said base, having a support for a model of an upper jaw, which support is mounted to pivot around a lateral shaft extending within a fixture which is universally movable relative to said base, having further a pressing means including a spring and acting along an axis extending perpendicularly to said lateral shaft and operative to press said base and said fixture at their respective supporting surfaces together such that due to a form closed abutment of base and fixture at said supporting surfaces a defined relative position between base and fixture is reached, which said pivotable support for a model of an upper jaw is movably guided relative to said base by means of a cam and a cam follower, which said support for a model of an upper jaw is carried in a pivoting arm supported by means of said lateral shaft in a bearing pedestal, said bearing pedestal and said pivoting arm forming together said fixture.

2. Description of the Prior Art

An articulator of the kind set forth above is disclosed in the Swiss patent specification No. 412 194. If the clamping means of this known articulator is in a released state, the fixture and base thereof will be moved by a spring arranged within the clamping means out of a respective form closed locked position such that the fixture may be spherically moved relative to the base. Such allows obviously a movement along the three spatial axes as well as a combination of these movements; however, a natural chewing movement (articulation) cannot be simulated because the lower jaw is obviously not mounted to the upper jaw via a spherical hinge. In order now to provide such articulators allowing the simulation of the natural chewing movements several developments have been made and disclosed such as disclosed for instance in the Swiss patent specification Nos. 346 319, 350 757; 437 629; 515 031 and 604 675. All these named articulators referred to above have in common the provision of two sockets of respective ball-and-socket joints located on a lateral axis and the distance between the two joint sockets is claimed to correspond to the distance of the natural joint sockets of human beings. According to an embodiment disclosed mentioned distance between the two sockets amounts to 108 mm. Conclusively, the articulators disclosed are quite bulky, necessitate due to the requisite precision an expensive steel construction, a meeting of close tolerances and, therefore, feature a relatively complicated and expensive structural conception. The above described drawbacks of the articulators of the other design are claimed to be overcome by the above referred articulator in accordance with the Swiss patent specification No. 412 194.

SUMMARY OF THE INVENTION

It is a general object of the present invention to provide an improved articulator incorporating the advantages of the two above mentioned articulator designs without having mentioned drawbacks.

A further object of the invention is to provide an improved articulator, in which the pivoting arm is guided movably relative to the bearing pedestal and laterally to the lateral shaft against the force of a second spring, and in which the cam and the cam follower are located between the pivoting arm and the base.

Yet a further object is to provide an articulator having a simple and compact construction such as is disclosed in the Swiss patent specification No. 412 194, yet having the ability to simulate all possible natural chewing movements of the jaws (articulation), an articulation which hitherto was possible to be carried out by means of the other previously referred to executions of articulators having, as mentioned, the drawback of the large distance between the two hinge joints located at the lateral axis.

BRIEF DESCRIPTION OF THE DRAWINGS

This invention will be better understood and objects other than those set forth above will become apparent when consideration is given to the following detailed description thereof. Such description makes reference to the annexed drawings, wherein:

FIG. 1 illustrates a preferred embodiment of the articulator in accordance with the invention and designed roughly on a one to one scale;

FIG. 2 is a side view of the articulator illustrated in FIG. 1 at a position rotated by 90°;

FIG. 3 is a plan view of the articulator illustrated in FIGS. 1 and 2;

FIG. 4 is a plan view of a part of the articulator;

FIG. 5 is a view of the rear of the articulator; and

DESCRIPTION OF THE PREFERRED EMBODIMENT

Figure 6:
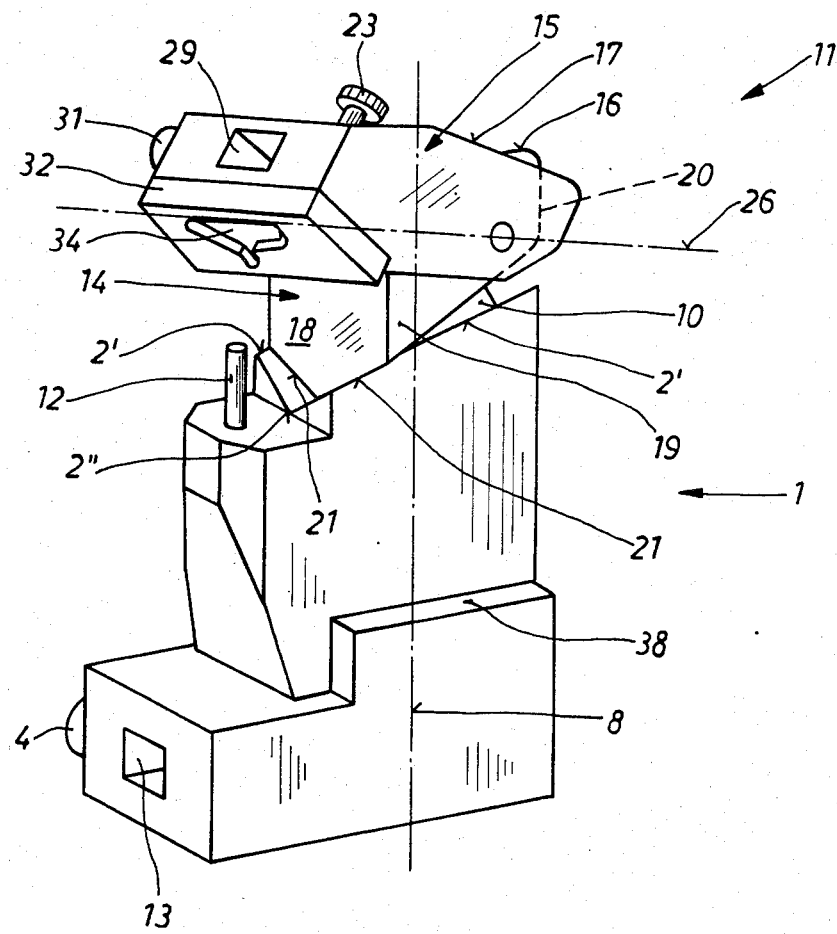
FIG. 6 is a perspective illustration of the articulator.

Describing now the drawings and considering initially the exemplary embodiment of an articulator as illustrated in FIG. 1 it will be understood that such articulator comprises a base 1 having an outer contour 2. A support 3 for a not particularly illustrated model of the lower jaw is held on this base by means of a set screw. The base 1 may be manufactured, for instance, from a plastic material. The base 1 is provided with a blind hole 5 and a through bore 6 arranged concentrically thereto and receiving an elongated shaft 8 movably guided in the base 1 against the force of a spiral pressure spring. Mentioned elongated shaft 8 can be fixably clamped at the base 1 by means of a clamping screw 9. The upper face surface of the base 1 is formed as supporting surface 10 for a fixture 11. This supporting surface 10 extends as is clearly shown in FIG. 2 from the contour 2′ to the contour 2″. These contours are also illustrated in FIGS. 1 and 5. This supporting surface 10 extends relative to the horizontal at an angle in the range of 15° to 25° such as illustrated in FIG. 2 and this preferred embodiment illustrated features an angle of 20°. The plane of occlusion between the model of the lower jaw and the model of the upper jaw not particularly shown in the figures extends in FIGS. 1 and 2 along a horizontal line such that accordingly the supporting surface 10 and its longitudinal sides, namely the contours 2′ and 2″, extend obliquely relative to said plane of occlusion at mentioned angle of 20° and extend from a low front location to a rear high location. The front side of the articulator is located in the illustration of FIG. 2 at the right hand side thereof. Additionally, the supporting surface 10 of the base 1 has a V-shaped extent such as illustrated in FIGS. 1, 5 and 6. The legs of this V-shape define together an angle in the range of 120° to 140° and the preferred embodiment shows an angle of 130°. The base 1 is provided, furthermore, with a vertically extending pin 12, which is operative as cam follower of a cam, as will be explained in detail further below. This pin 12 is made preferably from a metal. A metal guide bushing not shown may be inserted into an opening or recess, respectively, of base 1 and the support 3 can be inserted into such guide bushing. The rest of the base 1 can be fabricated, for instance, from nylon.

Next, the fixture 11 will be described. This fixture 11 is a two-piece structure comprising a bearing pedestal 14 and a pivot arm 15. The upper surfaces 16 and 17 of the bearing pedestal 14 and pivot arm 15, respectively, coincide if the articulator is located in the position as illustrated in FIGS. 1 and 2. The bearing pedestal 14 comprises, furthermore, outer surfaces 18, 19, 20 and 21. The surfaces 21 of the bearing pedestal 14 provide the supporting surfaces of the fixture 11 relative to the base 1 and, therefore, correspond to the supporting surfaces 10 of base 1. Accordingly, the supporting surfaces 21 of the fixture 11 are also arranged in a V-shaped fashion such that the angle enclosed is within the range of 120°–140°, in the particular illustrated embodiment 130°. In the position shown in FIGS. 1, 2 and 5 the supporting surfaces 10 and 21 of base 1 and fixture 11, respectively, abut each other in a form closed position and in the position of the articulator as illustrated in FIG. 6 they are out of such respective engagement. It shall be mentioned in this instance that the form closed condition of surfaces 10 and 21 is achieved by means of the spring 7 located at the elongated shaft 8 such that the position of the parts shown in FIG. 6 is arrived at against the action of the force of mentioned spring 7.

At the upper end of the bearing pedestal 14 a slanted surface 22 is provided and a set screw 23 located in the pivot arm 15 can be moved to abut the slanted surface 22. By means thereof the occlusion between lower jaw model and upper jaw model is set, i.e. the distance between the two jaw models can be altered. Mentioned elongated shaft including its thread 24 is screwed into the bearing pedestal 14 to have a locked seat. Accordingly, the spiral pressure spring 7 presses the bearing pedestal 14 including its supporting surfaces 21 against the supporting surfaces 10 of base 1 such that the defined position of fixture 11 relative to base 1 is arrived at by a form closed abutment of the V-shaped surfaces 10 and 21, which position is shown in FIGS. 1, 2 and 3. The elongated shaft 8 including its spring 7 acts as pressure means acting along the elongated shaft, by means of which the supporting surfaces 10 and 21 are pressed onto each other.

The rear end of the pivot arm 15 is forked such to provide legs 25 (FIG. 3). The bearing pedestal 14 located therebetween is received in this forked end and the legs 25 of the fork are guided at their inner surfaces at the outer surfaces 19 of the bearing pedestal 14. The pivot arm 15 is mounted to the bearing pedestal 14 via a lateral shaft 26, a longitudinal slot 27 and a second spring 28. The lateral shaft 26 is axially and radially locked relative to and in the pivot arm 15. The longitudinal slot 27 is located in the bearing pedestal 14 and the longitudinal slot 27 extends from a lower front position to a rear upper position marking an angle with the plane of occlusion in the range of 15° to 25°, the angle shown in this preferred embodiment amounts to 20°. Accordingly, now, this longitudinal slot 27 extends parallel to the slant of the supporting surfaces 10 and 21. The spiral pressure spring 28 used in this embodiment rests at the one end against the bearing pedestal 14 and the other end against the lateral shaft 26 (FIG. 3). Accordingly, the pivot arm 15 is movable relative to the bearing pedestal 14 against the force of this second spring 28 and during such movement the lateral shaft 26 is laterally shifted inside the longitudinal slot 27. During such movement of the pivot arm 15 relative to the bearing pedestal 14 mentioned moving or shifting, respectively, of the inner surfaces of the legs 25 of the fork relative to the outer surfaces 19 of the bearing pedestal 14 as shown in FIG. 3 is carried out. In place of the spiral pressure spring 27 a further embodiment foresees the use of a leaf spring (not particularly shown).

The pivot arm 15 is provided with a recess 29, in which recess 29 a support 30 for a not particularly shown upper jaw model can be inserted. This support 30 is mounted via a set screw 31 to the pivot arm 15 and accordingly mounted also to the fixture 11. The pivot arm 15 carries an exchangeable plate 32 which is mounted to the pivot arm 15 by means of pins inserted in holes 33. This plate 32 is provided with an inner cam surface 34 (see FIG. 4) having specifically two cam sections 35 and 36. This cam 34 is particularly shown in FIG. 4. The two unequally extending cam sections 35 and 36 extend obliquely to the horizontal line, each marking a separate angle therewith. The meaning of this design will be explained further below. The plane of occlusion 37 is illustrated in FIG. 2; according to FIG. 2 this plane of occlusion 37 extends horizontally between support 3 and support 30.

The elongated shaft 8 as well as the pin 12 (cam follower) extend perpendicularly thereto. The lateral shaft 26 extends parallel to the plane of occlusion 37. The plate 32 is mounted exchangeably at the pivot arm 15 such that it may be mounted also in such a position to the pivot arm 15 that according to the illustration of FIG. 4 the slanted cam section 35 may be located at the left hand side and the slanted cam section 36 at the right hand side of the opening illustrated therein. The prevailing chosen position of the plate 32 at the pivot arm 15 depends on a left or a right jaw model being carried by the articulator. FIG. 4 is a view in accordance with FIG. 2 from below against the plate 32. The position of the plate 32 at the pivot arm 15 as illustrated in FIG. 4 is the position prevailing when a left jaw model is to be carried by the articulator.

The fixture 11 is movable relative to the base 1 in all directions, i.e. along the three spatial axes. Relative to the movement of one axis the fixture 11 as shown in FIG. 2 is movable against the force of spring 7 in the direction coinciding with the plane defined by the drawing sheet. Perpendicularly thereto (again relative to FIG. 2) fixture 11 is movable against the spring 21 illustrated in FIG. 3 also in mentioned plane defined by the drawing sheet. The third spatial direction of movement is arrived at when fixture 11 is rotated around the elongated shaft 8 relative to the base 1, i.e. based on FIG. 2 in a plane extending perpendicularly to the plane defined by the surface of the drawing sheet. During latter movement the form closed condition between supporting surfaces 10 and 21 of base 1 and fixture 11 is obviated such as illustrated in FIG. 6. The three above explained freedoms of movement of the fixture 11 relative to the base 1 are controlled with regard to their components of movement by means of the cam 34 and the follower pin 12 such to simulate the natural chewing movement (articulation). In order to explain the various angles of the slanted cam sections 35 and 36 illustrated in FIG. 4 relative to the horizontal plane reference is made to the initially described design of articulators in which the two bearing sockets are located at a considerable distance from each other at the lateral axis. If now a left or a right jaw model is carried by such a previously known articulator, this left or right jaw model is not located in the center between the two joint sockets, it is rather located more towards the left joint socket or more towards the right joint socket such as obviously is also the case of the natural human head. The articulating movement between an upper and a lower tooth is, therefore, dependent on the location of such two teeth acting together relative to the two joint sockets between lower jaw and upper jaw. The specific position of the left jaw model or of the right jaw model relative to the two above mentioned joint sockets is now taken into consideration by the two from each other differing slanted cam sections 35 and 36. If a left lower jaw model or upper jaw model is processed with aid of the illustrated articulator, the fixture 11 will be moved such relative to the base 1 that the slanted cam sections 35 and 36 are moved along the follower pin 12. The pivot arm 15 is thereby moved against the force of spring 28 relative to the bearing pedestal 14 and the bearing pedestal 14 in turn is moved relative to base 1. FIG. 6 illustrates such a rotated position of the bearing pedestal 14 relative to base 1, in which illustration, however, due to an easier understanding the pivot arm 15 is designed such that its cam 34 is moved away from the follower pin 12, i.e. it has been designed in an opened, swung out pivot position and not in the closed position as obviously is the case during practical operation.

The illustrated articulator can also be designed such, that the height of the base 1 can be changed. This embodiment is not illustrated. Such can, for instance, be arrived at easily in that the base 1 is made of two separate parts in that the base 1 is divided in a horizontal plane relative to FIG. 2, which two parts can be pushed together or pulled apart by means of guide pins extending vertically with reference to FIG. 2 and not shown. In order to block this possibility of relative movement of the two parts, a further set of screws could be provided, which set of screws would act directly onto the guide pins.

The articulator described herein has its application mainly for fractional impressions (mashing bites), can, however, also be used for complete impressions. The inventive articulator is designed such that when carrying out fractional impressions the simulation of the chewing movements of the complete jaw on the left or right lateral teeth (molars) up to the canine-tooth can be simulated in spite of the missing two joint sockets located at the lateral axis and at a mutual distance from each other. By means of a simple rearranging of the plate 32 as set forth above the chewing movements of the left or of the right joint of the jaw can be simulated. The angle which the slanted cam section 35 marks with the horizontal line and the angle of the slanted cam section 36 relative to the horizontal line shown in FIG. 4 are based on the mean value of the angle of movement of the human jaw joint. The slanted cam section 35 of FIG. 4 marks with the horizontal line an angle of 20° and the slanted cam section 36 marks with the horizontal line an angle of 57°.

According to a further embodiment the exchangeable plate may also be fixed to the base 1, in which case the follower pin 12 is mounted to the pivot arm. According to a still further embodiment the curve, i.e. cam 34, can have a different shape such that it is not necessary to flip the plate 32 over as mentioned above but rather to rotate the plate 32 in its plane.

The set screws 4, 9 and 31 illustrated in FIGS. 1 and 2 are not illustrated in FIGS. 3 and 5. The plane of occlusion 37 corresponds with the plane defined by the surface 38 of base 1.

I claim:

1. An improved articulator having a base including a support for a model of a lower jaw, said support carried by said base, having a support for a model of an upper jaw, which support is mounted to pivot around a lateral shaft extending within a fixture which is universally movable relative to said base, having further a pressing means including a spring and acting along an axis extending perpendicularly to said lateral shaft and operative to press said base and said fixture at their respective supporting surfaces together such that due to a form closed abutment of base and fixture of said supporting surfaces a defined relative position between base and fixture is reached, which said pivotable support for a model of an upper jaw is movably guided relative to said base by means of a cam and a cam follower, which said support for a model of an upper jaw is carried in a pivoting arm supported by means of said lateral shaft in a bearing pedestal, said bearing pedestal and said pivoting arm forming together said fixture;

in which said pivoting arm is guided movably relative to said bearing pedestal and laterally to said lateral shaft against the force of a second spring, and in which said cam and said cam follower are located between said pivoting arm and said base.

2. The improved articulator of claim 1, in which the respective supporting surfaces of the base and of the bearing pedestal extend obliquely from a low front to a high rear position marking an angle of 15°–25° relative to the plane of occlusion.

3. The improved articulator of claim 1, in which the supporting surfaces of the base and of the bearing pedestal have a V-like shape, the legs thereof enclosing an angle in the range of 120°–140°.

4. The improved articulator of claim 1, in which the lateral shaft is laterally movable within a longitudinal slot extending from a low front to a high rear position marking an angle of 15°–25° relative to the plane of occlusion.

5. The improved articulator of claim 1, in which the cam follower comprises a pin extending together with the longitudinal axis in a common plane.

6. The improved articulator of claim 1, in which said cam is formed by an inner wall section of an opening in an exchangeable plate, which plate is mountable on the fixture in two positions, in accordance with a left or right jaw model being supported by the articulator.

7. The improved articulator of claim 6, in which the exchangeable plate is mounted to the pivotable arm and is pivotable into a plane which extends parallel to the plane of occlusion, and in which the cam follower is a pin extending laterally relative to the plane of occlusion.

8. The improved articulator of claim 4 having a lateral shaft which is mounted in the pivoting arm in an axially and radially locked condition, wherein said second spring rests at one of its ends against the lateral shaft and at the other end against the bearing pedestal, and wherein the longitudinal slot is located in the bearing pedestal allowing a moving of the lateral shaft in the slot against the force of the spring and from a low front to a high rear position.

9. The improved articulator of claim 1, in which the base can be altered in its height.

* * * * *